United States Patent [19]

Prutchi et al.

[11] Patent Number: 5,730,125
[45] Date of Patent: Mar. 24, 1998

[54] IMPLANTABLE MEDICAL DEVICE WITH ENCLOSED PHYSIOLOGICAL PARAMETER SENSORS OR TELEMETRY LINK

[75] Inventors: David Prutchi; Patrick J. Paul, both of Lake Jackson, Tex.

[73] Assignee: Sulzer Intermedics, Inc., Angleton, Tex.

[21] Appl. No.: 712,280

[22] Filed: Sep. 11, 1996

Related U.S. Application Data

[62] Division of Ser. No. 392,181, Feb. 22, 1995, Pat. No. 5,556,421.

[51] Int. Cl.⁶ ................................................ A61N 5/08
[52] U.S. Cl. ........................................ 128/637; 607/22
[58] Field of Search .................................. 128/637, 664, 128/665, 689, 661.08; 607/22

[56] References Cited

U.S. PATENT DOCUMENTS

| | | | |
|---|---|---|---|
| 4,730,389 | 3/1988 | Baudino et al. | 29/825 |
| 4,750,495 | 6/1988 | Moore et al. | 128/419 |
| 4,807,629 | 2/1989 | Baudino et al. | 128/419 |
| 4,813,421 | 3/1989 | Baudino et al. | 128/633 |
| 4,860,751 | 8/1989 | Callaghan | 128/419 |
| 4,903,701 | 2/1990 | Moore et al. | 128/419 |
| 4,945,909 | 8/1990 | Fearnot et al. | 128/419 |
| 5,014,700 | 5/1991 | Alt | 128/419 |
| 5,014,702 | 5/1991 | Alt | 128/419 |
| 5,014,703 | 5/1991 | Alt | 128/419 |
| 5,014,704 | 5/1991 | Alt | 128/419 |
| 5,312,454 | 5/1994 | Roline et al. | 607/22 |
| 5,355,893 | 10/1994 | Mick et al. | 128/664 |
| 5,390,670 | 2/1995 | Centa et al. | 128/633 |
| 5,423,869 | 6/1995 | Poore et al. | 607/18 |
| 5,431,170 | 7/1995 | Mathews | 128/666 |

FOREIGN PATENT DOCUMENTS

| | | |
|---|---|---|
| 0580128 | 1/1994 | European Pat. Off. |
| 9118550 | 12/1991 | WIPO |

*Primary Examiner*—Scott M. Getzow
*Attorney, Agent, or Firm*—Conley, Rose & Tayon, P.C.

[57] ABSTRACT

An implantable medical device, such as a cardiac pacer, defibrillator or drug delivery system, includes a container housing the required power source and circuitry and a header portion molded or glued to the container housing. Sensors, including physiological parameter sensors as may be necessary to control and implement the operation of the implantable device, or a telemetry link, or both, are disposed and sealed within the header. The header may include electromagnetic focusing devices to enhance the performance of the sensors. The sensors may include two pulse oximetry sensors that provide differential measurements to improve detection of arterial blood flow.

26 Claims, 9 Drawing Sheets

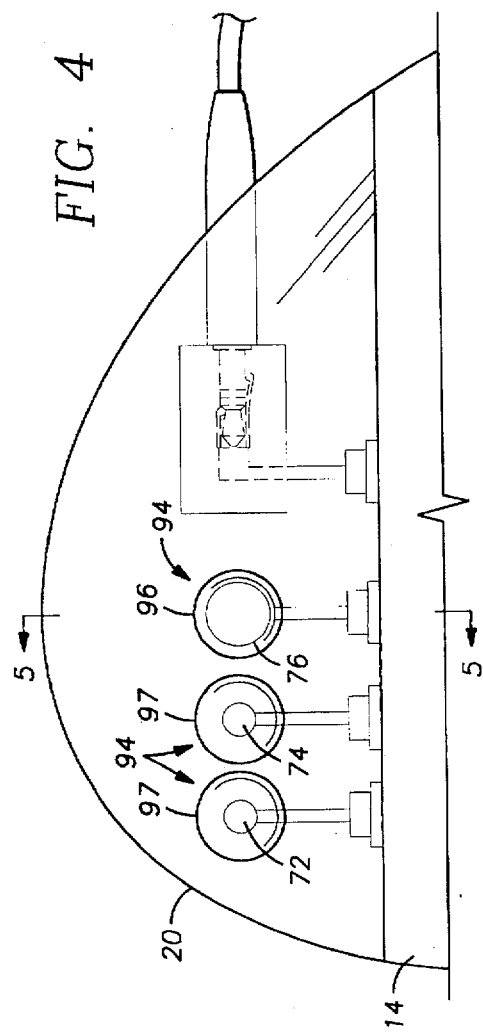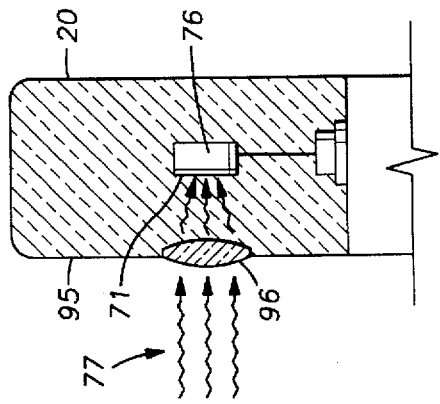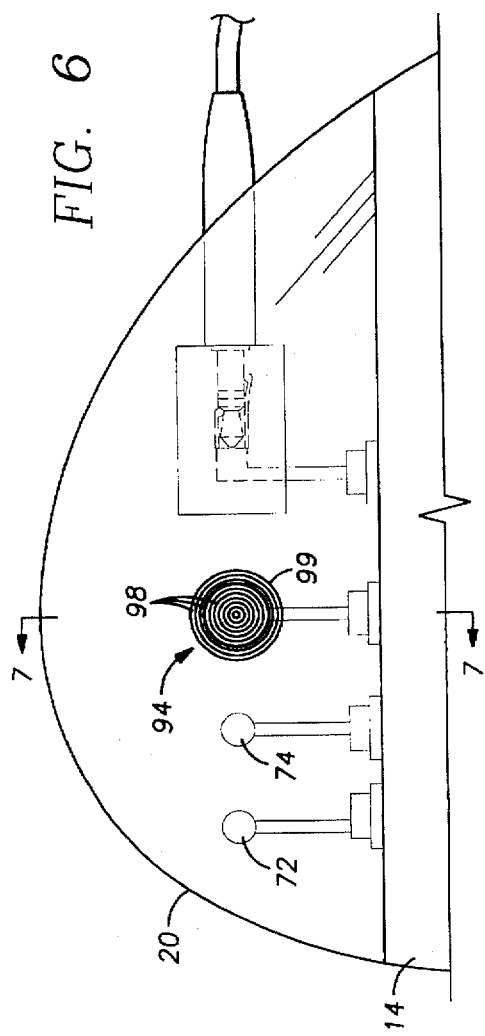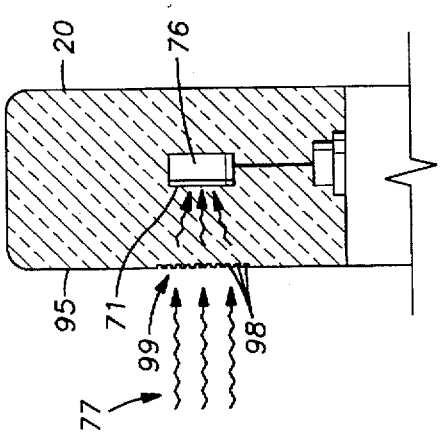

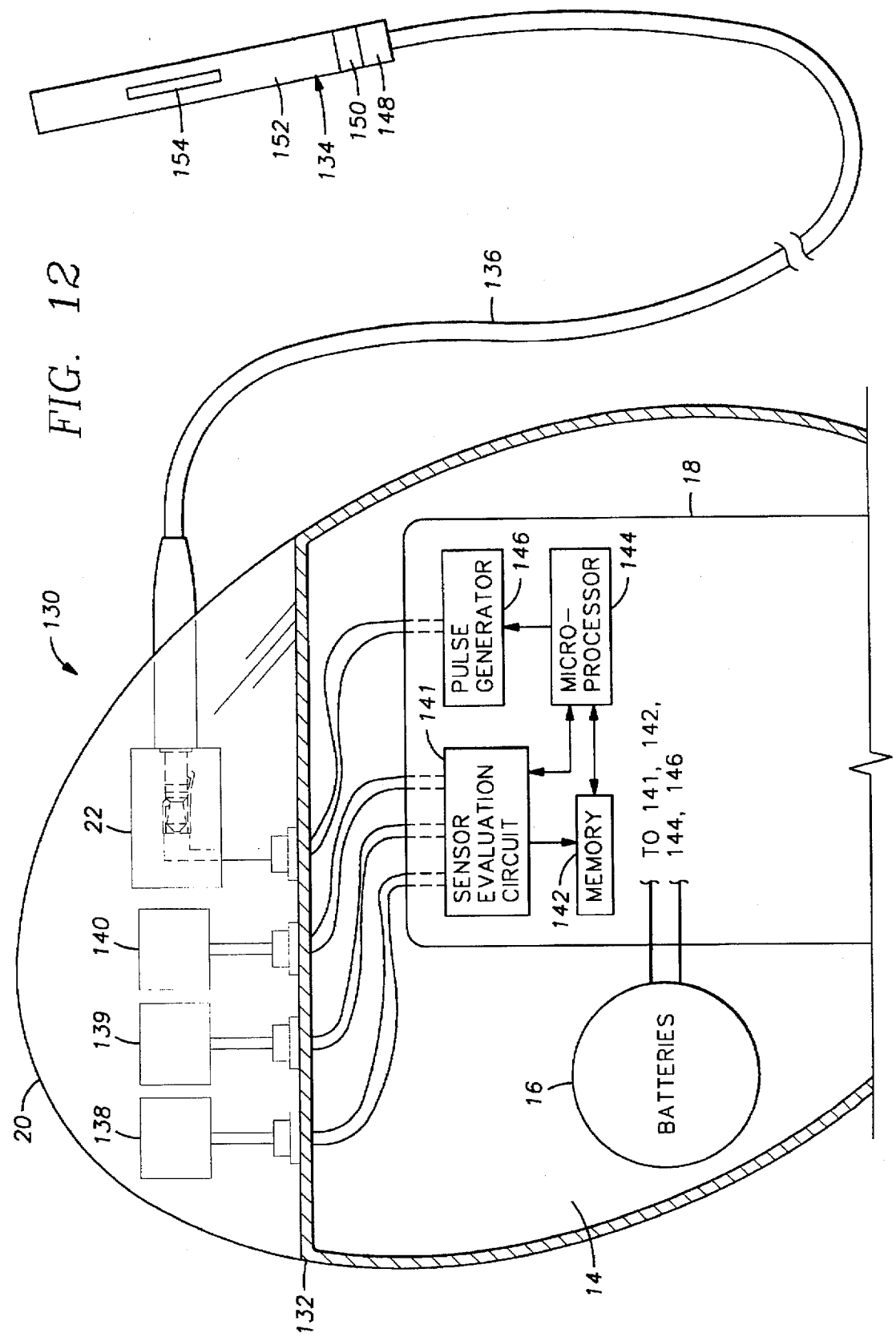

IMPLANTABLE MEDICAL DEVICE WITH ENCLOSED PHYSIOLOGICAL PARAMETER SENSORS OR TELEMETRY LINK

This is a divisional of U.S. patent application Ser. No. 08/392,181 filed Feb. 22, 1995 now U.S. Pat. No. 5,556,421.

FIELD OF THE INVENTION

The present invention relates generally to implantable medical devices, such as cardiac pacemakers, defibrillators and any of a variety of drug delivery systems. More particularly, the invention relates to such implantable treatment devices in which telemetry transducers or physiological parameter sensors are contained and sealed within the header of the implantable device.

BACKGROUND OF THE INVENTION

Implantable medical devices having electrical circuit components are well known in medical science. Some of the most common forms of such implantable devices are pacemakers and defibrillators. Additionally, implantable drug delivery systems are available for supplying needed medication for treatment of disease or for responding to the physiological demands of a patient in an emergency situation.

A pacemaker (or "pacer" as it is commonly labelled) is an implantable medical device which delivers electrical pulses to an electrode that is implanted adjacent the patient's heart in order to stimulate the heart so that it will beat at a desired rate. A normal human heart contains a natural pacemaker by which rhythmic electrical excitation is developed. If the body's pacemaker performs correctly, blood is oxygenated in the lungs and efficiently pumped by the heart to the body's oxygen-demanding tissues. However, when the body's natural pacemaker malfunctions, due to age or disease, an implantable pacemaker often is required to properly stimulate the heart. An in-depth explanation of certain cardiac physiology and pacemaker theory of operation is provided in U.S. Pat. No. 4,830,006.

In recent years, "rate-responsive" pacemakers have been developed which, in response to a sensed physiological parameter, will automatically change the rate at which the pacemaker provides stimulating pulses to the heart. The physiological parameter provides some indication of whether the heart rate should increase or decrease, as dictated by the physiological needs of the patient. For example, where the patient is at rest, the rate-responsive pacemaker will maintain a normal or base rate of, for example, 60–70 pulses per minute. However, if the sensed physiological parameter indicates that the patient is exercising, then there is a need for the heart to beat much faster, and the pacemaker will respond by stimulating the heart to beat at a higher rate, for example, 100–110 beats per minute.

Similarly, implantable defibrillators sense physiological parameters in order to determine when to supply a defibrillating shock to a patient's heart. Ventricular fibrillation is a condition characterized by rapid, chaotic electrical and mechanical activity of the heart's excitable myocardial tissue, and results in an instantaneous cessation of blood flow from the heart due to the uncoordinated or ineffectual action of the ventricles. Defibrillation is a technique employed to terminate fibrillation by applying one or more high energy electrical pulses to the heart in an effort to overwhelm the chaotic contractions of individual tissue sections and to restore the synchronized contraction of the total mass of tissue.

Likewise, implantable drug delivery systems also may rely upon physiological parameter sensors to provide signals that may be processed internally in order to determine when, and in what amount, a stored drug is to be delivered into the patient's body. In the treatment of certain diseases, it is desirable to administer a drug into a particular location within the body where the drug will be most effective in combating the localized disease. As another example, in treating cardiac arrhythmias, it is sometimes desirable to deliver the drug directly to the heart. In other applications of implantable drug delivery systems, the location at which the drug is introduced into the body is not critical, and the body's circulatory system is relied on to carry the administered drug to all parts of the body. Drugs that may effectively be administered by implantable delivery systems include insulin, glucose, heparin or any of a variety of chemotherapeutic agents.

Because the condition requiring the use of an implantable device may drastically impair the patient's quality of life or, in some instances, is a life threatening condition, having reliable indicators of physiological parameters is imperative. Physiological parameter sensors and activity parameter sensors that have been employed in association with implantable devices, or that those in the art have suggested may be employed, include those that sense respiration rate, blood oxygen saturation level, temperature, blood pressure, pH, length of the Q-T interval, the length of the P-R interval, thoracic impedance changes, nerve activity, biochemical concentrations (such as enzymes and glucose) and motion or acceleration.

Regardless of the sensed parameter, most prior art implantable devices have relied upon physiological parameter sensors that are positioned remotely from the implantable device. For example, U.S. Pat. No. 4,886,064 discloses sensors that are implanted remotely from a pacemaker and that wirelessly transmit to the pacemaker signals that indicate or correlate to a sensed parameter. In many other prior art implantable devices, however, the remote sensors are interconnected with the implantable device by means of electrical leads or conductors that are encased in a catheter that extends between the remote sensor and the implantable device. For example, U.S. Pat. No. 4,903,701 discloses an oxygen sensor that is located remotely from the pacemaker and that is mounted on the electrical leads used to transmit the generated pulse from the pacemaker to the stimulating electrode. U.S. Pat. No. 4,763,655 discloses a temperature sensor and a blood oxygen sensor that are implanted remotely from the pacemaker housing. The sensors are coupled with the pacemaker circuitry by conductors encased in a catheter.

Designs for implantable devices that rely upon remote sensors pose significant problems. First, radiofrequency transmission, as suggested by U.S. Pat. No. 4,886,064, typically requires transmitters and receivers that substantially increase the volume, weight and complexity of the pacemaker and sensor. These characteristics are generally undesirable in an implantable device where, for patient comfort, small size and light weight packages are desired goals. Second, remote sensors often need specialized catheters and are susceptible to fixation and migration problems. Another drawback of employing remotely-positioned sensors, at least those that are implanted within or adjacent to the patient's heart, is that should such a sensor fail, delicate surgical intervention may be required to remove and replace the faulty sensor. By contrast, pacemakers and many other implantable devices are typically positioned in an easily accessible location just beneath the patient's skin, and can be accessed and replaced without the risk of life-threatening or extremely costly surgery. Also of significance, because of the required electrical connections between the remote sensors and the internal circuitry within the implantable device, the device is susceptible to infiltration by corrosive body fluids. Any such infiltration will almost instantaneously disable the electrical circuitry in the device. Thus, the locations at which the sensor's leads penetrate the housing of the implantable device must be sealed to prevent infiltration of body fluids.

Those involved in the medical arts already have confronted the problem of preventing fluid from infiltrating into an implantable device at the locations where external leads attach to the device housing. As mentioned previously, it is conventional practice to surgically implant a stimulating electrode adjacent the heart and to interconnect the electrode to the pacemaker via conducting leads. This arrangement is shown, for example, in U.S. Pat. No. 4,903,701. Additionally, certain implantable medication delivery systems require that electrical conductors interconnect an implantable device containing a power source and control circuitry and a remotely positioned drug dispensing device as, for example, disclosed in U.S. Pat. No. 5,041,107. It is, of course, important that all such leads be securely attached to the implantable device to prevent the leads from becoming inadvertently decoupled. At the same time, because pacemakers and drug delivery systems require periodic replacement, and because this replacement procedure ideally is accomplished without disturbing any remotely implanted electrode or other device, the connections between the leads and the implantable device housing must be readily disconnectable. It is critical, of course, that the lead termination and attachment mechanisms prevent infiltration of any fluids into the implantable device.

To date, it has been common in the design of implantable devices to provide the device with a header portion which includes one or more terminals for landing and terminating any external leads. The header, which may be made of an epoxy material, supports and insulates the terminals. Internal conductors interconnect the terminal in the header portion with the electrical circuitry contained within the housing of the implantable device. Examples of such headers are shown in U.S. Pat. Nos. 5,282,841 and 4,072,154. Where physiological parameter sensors (rather than electrodes) are implanted remotely from the implantable device, similar such termination means must be provided for landing and terminating the conductors that communicate signals between these remote sensors and the implantable device.

In part due to the various problems and disadvantages of positioning sensors remotely from the pacemaker or drug delivery device with which they are associated, it has been suggested that the sensors be housed within the implantable treatment device itself. For example, U.S. Pat. No. 5,040,533 proposes an implantable cardiovascular treatment device having self-contained sensors and a window formed in the wall of the container to permit the sensors that are housed within the container to detect or measure a physiological parameter through the window. Although proposed as a solution to some of the aforementioned problems associated with external sensors, the "windowed" pacemaker presents additional and even more pronounced sealing problems. Because the interface between the window and the walls of the container must prevent infiltration by body fluids, a complete and enduring seal must be devised and installed along the entire perimeter of the window. Providing such a seal in the walls of the container presents significant manufacturing difficulties, especially considering the small size of the container that is typically employed in pacemakers. Further, the additional components and manufacturing time and effort that are needed to provide such a sealed window in the walls of the implantable device would increase substantially the cost of manufacturing such a device.

Thus, despite significant advances in the art that have been made over the years, there remains a need for an implantable device capable of housing and protecting any of a variety of types of physiological parameter sensors. The device must permit the sensors to carry out their intended functions and, simultaneously, must seal the devices from exposure to corrosive body fluids. Especially well received would be an implantable device that would be no larger than those presently employed and that would not require significant additional retooling in order to manufacture a new and specialized housing, such as one requiring that a window be formed in what would otherwise be a continuous wall. Ideally, the new device would not create additional sealing problems and could employ known and reliable electrical power supplies and circuitry. Preferably, the implantable device would also house a telemetry link through which data and instructions could be communicated to and from the implantable device.

SUMMARY OF THE INVENTION

In accordance with the present invention, there is provided an implantable medical device having a container for housing electrical circuitry and a header that closes and seals the container. One or more sensors, which may be physiological parameter sensors or telemetry transducers, or both, are retained and sealed within the header.

The composition of the header is, in part, dependent upon the particular sensor employed. That is, the material from which the header is formed must allow the sensor to detect or measure through the header the desired physiological parameter. Depending upon the particular sensor, the invention may include a header formed of epoxy, plastic, glass or ceramic. The invention also may include electromagnetic focusing devices that are formed on or attached to the header to improve or enhance sensor performance.

Depending upon the desired application for the implantable device, the invention may include any of a variety of sensors that are presently available or that may become available for detecting or measuring relevant physiological parameters. In certain applications, such sensors may include photoemitters or photodetectors. In one particular embodiment of the invention, such photoemitters and detectors are arranged to comprise an oximetry sensor for detecting blood oxygen saturation. A particularly advantageous form of the invention employs two oximetry sensors that are positioned within the header so that their respective photodetectors face in different directions. This arrangement yields separate signals which can be processed in a way to eliminate the deleterious effects that movement may have on the ability of a single oximetry sensor to make the desired measurement of oxygen saturation of the arterial and mixed venous blood flows. In embodiments of the invention that employ such photodetectors, the invention will include a translucent or transparent header, for example a header made from a material that is transparent to wavelength in the infra-red and red portions of the optical spectrum.

In another embodiment of the invention, the header includes sensors that are capacitively or resistively coupled to the fluid and tissue outside the housing. Such sensors include a conductive plate disposed in the header a predetermined distance from the outer surface of the header. In embodiments of the invention including capacitively coupled sensors, the header may be formed of a material having a high dielectric constant and low volume resistivity, such as, for example, a dielectric constant of 3.8 and a volume resistivity greater than $1\times10^{13}$ ohm-cm. Where the sensors are resistively coupled, selected portions of the header may have a low volume resistivity of less than $1\times10^{6}$ ohm-cm.

Without regard to the type of sensor, the invention may be employed in pacemakers, defibrillators or implantable drug delivery systems. In these implantable devices, the invention includes a sensor evaluation circuit to receive signals from the sensor that are indicative of the measured physiological parameter. The invention further includes within the container a control circuit, such as a microprocessor, and an output circuit. The output from the sensor evaluation circuit is received by the control circuit which, in accordance with a predetermined algorithm, will signal the output circuit, such as a pulse generator, to generate an electrical pulse of a duration and magnitude required for properly stimulating the heart or dispensing an appropriate dose of medication.

The present invention having self-contained sensors eliminates the risky or dangerous surgical intervention that may otherwise be required to remove remotely positioned sensors, which fail. Further, because the invention takes advantage of a header such as that typically employed in present day pacemakers, the tried-and-true arrangement used in sealing conventional pacemakers may also be used when implementing the present invention. Likewise, no specialized housing or container for the implantable device circuitry is required when practicing the invention. Instead, conventional components and manufacturing techniques may be employed, and no additional interfaces are created which require complicated or costly seal designs.

Accordingly, the present invention comprises a combination of features and advantages which enable it to substantially advance the technology associated with implantable medical treatment devices. The characteristics and advantages of the present invention described above, as well as additional features and benefits, will be readily apparent to those skilled in the art upon reading the following detailed description and referring to the accompanying drawings.

BRIEF DESCRIPTION OF THE DRAWINGS

For a detailed description of the preferred embodiments of the invention, reference will now be made to the accompanying drawings wherein:

FIG. 4 is a partial elevation view showing another alternative embodiment of the present invention.

FIG. 5 is a sectional view taken along line 5—5 in FIG. 4.

FIG. 6 is a partial elevation view showing another alternative embodiment of the present invention.

FIG. 7 is a sectional view taken along line 7—7 in FIG. 6.

FIG. 12 is an elevational view of another alternative embodiment of the present invention as employed in an implantable iontophoretic drug delivery system.

DESCRIPTION OF THE PREFERRED EMBODIMENTS

Figure 1:
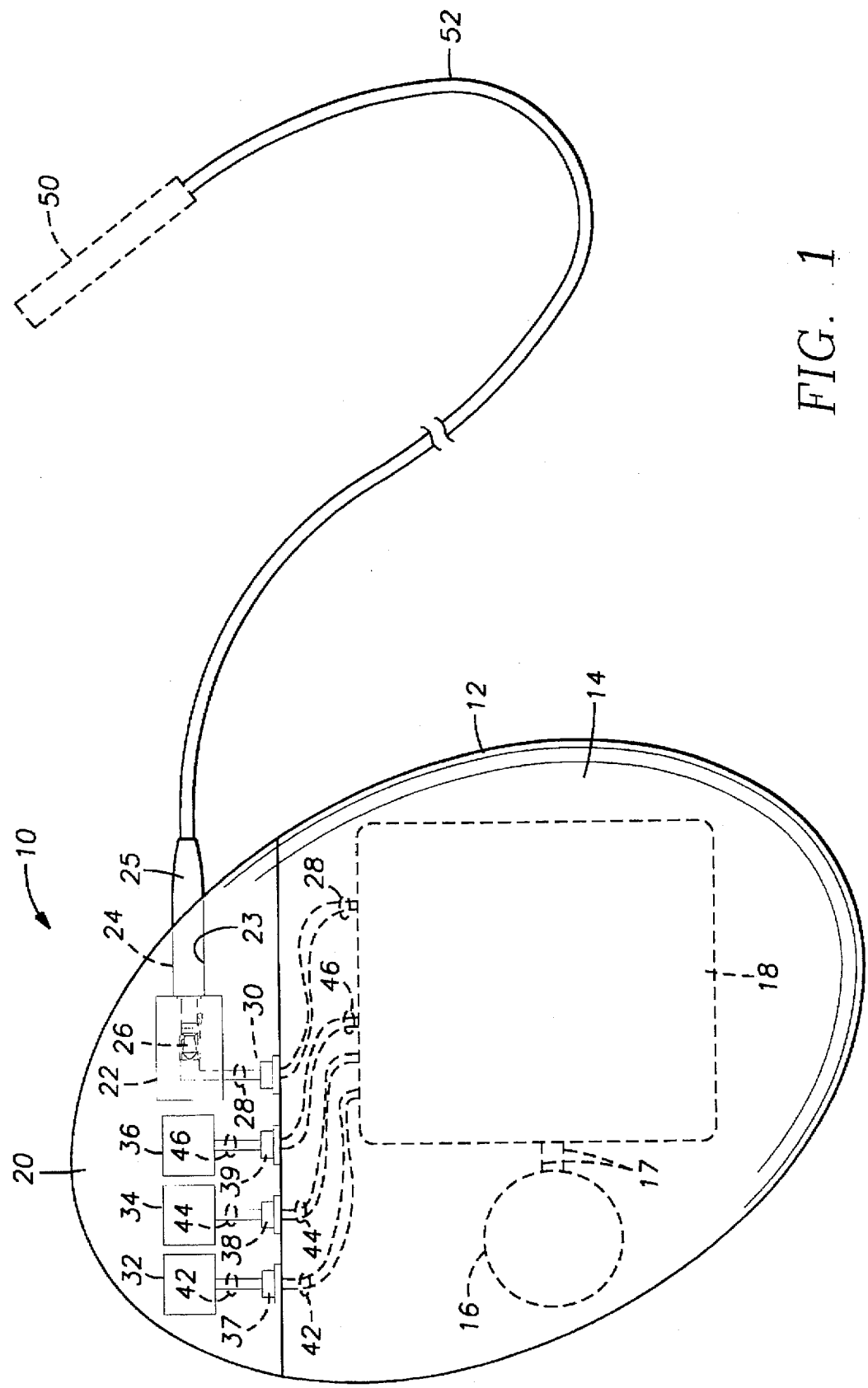
FIG. 1 is an elevational view of a pacemaker made in accordance with the present invention.

Presently-preferred embodiments of the invention are shown in the above-identified figures and described in detail below. In describing these various embodiments, like or identical reference numerals are used to identify common or similar elements.

Referring now to FIG. 1, there is shown an implantable device 10 which, in the embodiment shown in FIG. 1, is adapted for use as a self-contained implantable cardiac pacer 12. Pacer 12 comprises a can or housing 14 which contains an electrical energy source, such as battery 16, and a hybrid circuit 18 which includes electrical circuitry for generating an electrical pulse to stimulate a patient's heart in a predetermined manner. Pacer 12 further includes a header 20 which is molded or glued to housing 14 and serves as a termination point for the electrical conductors that are used to transmit the generated pulse to the patient's heart.

Imbedded within header 20 is terminal 22 and physiological parameter sensors 32,34,36. Terminal 22 is electrically interconnected with the hybrid circuitry 18 by conductors 28 which pass through conventional feedthrough 30. Similarly, sensors 32,34,36 are interconnected to the sensor circuitry 62 (FIG. 2) contained on the hybrid circuit 18 via conductors 42,44,46. It is to be understood that conductors 42,44 and 46 shown in FIG. 1 may each comprise two, three or more discrete conductors depending upon the requirements of the particular sensor employed. Conductors 42,44 and 46 pass from header 20 into housing 14 via feedthroughs 37,38 and 39, respectively. The battery 16 is interconnected with the hybrid circuitry 18 via conductors 17 in a conventional manner.

An electrode 50 used to stimulate the heart is interconnected with pacer 12 via conductors (not shown) that are sheathed in a flexible catheter 52. The proximal end of the conductors contained within catheter 52 terminate at connector 24 which includes a male connector pin 26. Pin 26 is inserted into terminal 22 within header 20 so as to electrically interconnect electrode 50 with the pulse generation circuitry contained the hybrid circuit 18. The elements used to interconnect external electrode 50 with circuitry within pacer 12 are conventional and well understood by those skilled in this art. Further details concerning such interconnections are shown, for example, in U.S. Pat. Nos. 5,076,270 and 4,860,750, the disclosures of which are incorporated herein by this reference. Connector 24 includes an outer covering 25 of silicon rubber or another material which is both resilient and insulative. Likewise, catheter 52 is covered with an insulative material throughout its length for insulating the electrical conductors that are contained therein.

Pacer housing 14 is made of a biocompatible, corrosion-resistant metal such as stainless steel or titanium. The header 20 preferably mounts on a welded housing 14 after the hybrid circuit 18 and battery 16 are assembled within the interior of the housing according to conventional techniques.

Header 20 may be formed from any of a large number of biocompatible materials capable of retaining and insulating sensors 32,34 and 36 and terminal 22. Header 20 must also have a transmissivity for electromagnetic energy as required by the particular sensor or communication mechanism employed in the implantable device 10. The header 20 therefore must be constructed of a suitable material that conducts electromagnetic energy without excessive absorption or reflection, thereby allowing the embedded sensor to transmit and receive electromagnetic energy to and from a point external to the header 20. For many applications, header 20 preferably is made of an epoxy resin or similar thermosetting polymer material which is formed in situ over terminal 22 and sensors 32,34 and 36. Header 20 is formed so as to include a bore 23 for receiving connector 24. Accordingly, sensors 32,34,36, terminal 22, as well as portions of conductors 28,42,44 and 46 are supported and imbedded within the cured resin, which also serves to insulate the encapsulated components. In addition to epoxy, other material suitable for header 20 include glass, plastics and elastomers, such as Dow Chemical's Pellethane and ceramic materials such as sapphire.

Figure 2:
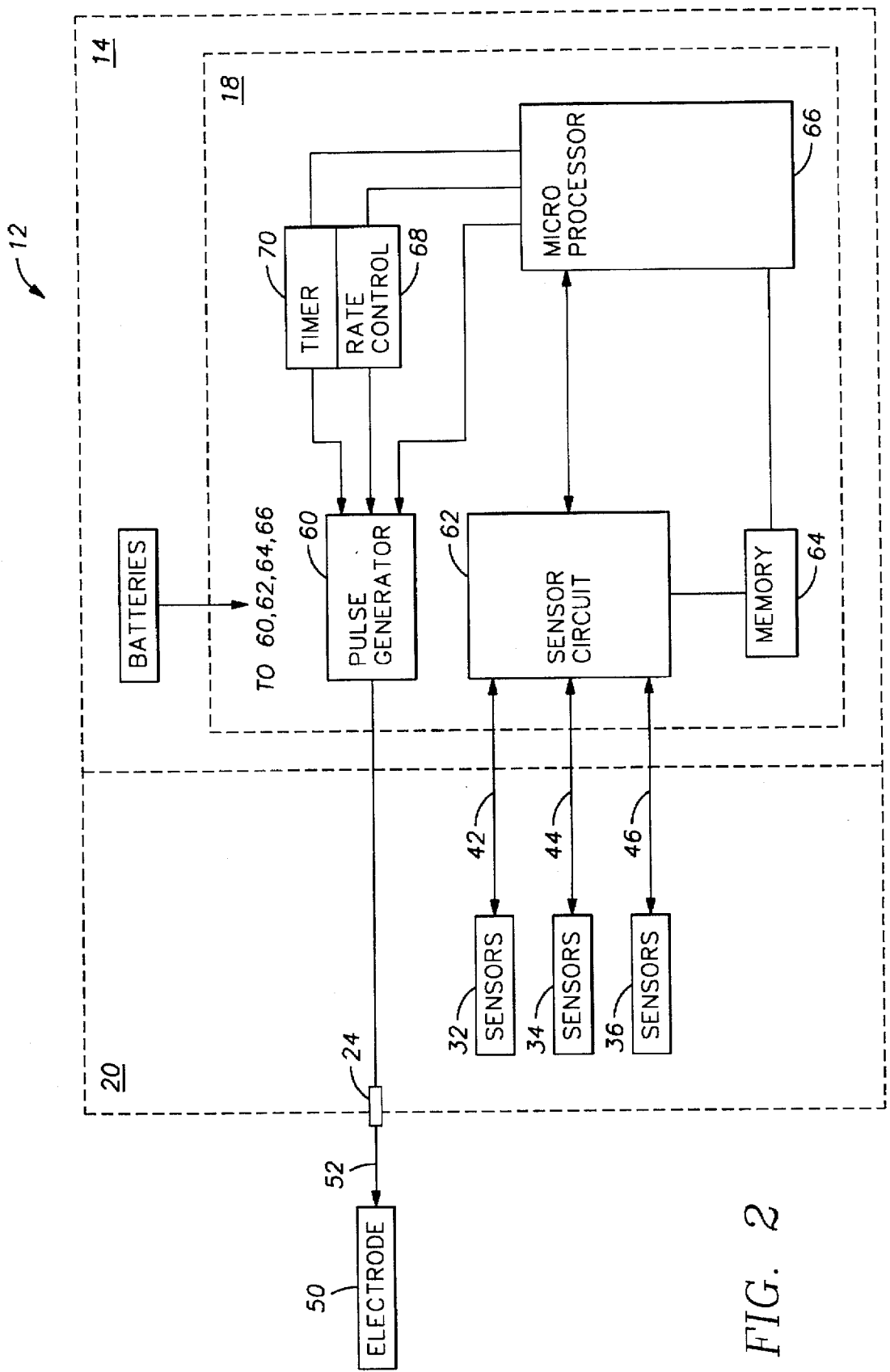
FIG. 2 is a schematic block diagram of the pacemaker shown in FIG. 1.

Referring now to FIG. 2, the various circuits mounted on hybrid circuit 18 and employed in this embodiment of the invention are shown in block diagram form. As shown, included on the hybrid circuit 18 is pulse generation circuitry 60 for generating the electrical pulse which is delivered through pacing electrode 50 for stimulating the patient's heart. Any of a variety of pulse generation circuits can be employed in the present invention including, for example, those disclosed in U.S. Pat. Nos. 5,318,596, 5,040,534 and 4,830,006, the disclosures of which are incorporated herein in their entireties by this reference. It should be understood, however, that the present invention is not limited to any particular pulse generation circuit.

Hybrid circuit 18 further includes sensor circuitry 62 for controlling, receiving, conditioning and processing the signals sent to and received from sensors 32,34 and 36, which are disposed within header 20. The sensor evaluation and control circuitry 62 also includes the components necessary to supply power to the sensors 32,34,36 and, as shown and described with reference to FIG. 3 below, may provide the control and logic necessary to time when various data are gathered or received. A memory circuit 64 also is mounted on the hybrid circuit 18 for storing various data, such as baseline data and algorithms which may be preprogrammed into memory circuit 64 or which may be programmed through an external programmer. A microprocessor 66 also is preferably included for receiving data from sensor evaluation and control circuitry 62 and for controlling the rates at which pulses are generated by pulse generator 60. Timer 69 and rate controller 68 are also included in the hybrid circuit 18 and interconnected between microprocessor 66 and pulse generator 60. Together, microprocessor 66, rate controller 68 and timer 69 cooperate to increase and decrease the rate that pulses are generated by pulse generator 60 in accordance with a predetermined schedule of rate increases or decreases that are preprogrammed into microprocessor 66. Rather than including discrete circuits for timer 69 and rate controller 68, these circuits preferably may be combined in a single integrated circuit package with microprocessor 66.

Sensors 32,34 and 36 are interconnected to sensor evaluation and control circuitry 62 via conductors 42,44,46 (FIG. 1). When employed in pacer 12, sensors 32,34 and 36 may be any of a variety of sensors capable of sensing various physiological parameters whose value correlate to heart rate. As previously discussed, the physiological parameters that may be sensed by implantable device 10 and evaluated for use in stimulating the heart, providing a defibrillizing pulse or dispensing needed medication include, for example, blood oxygen saturation, respiration rate, pulse rate, temperature, pH value of the blood, the natural atrial rate and the QT interval.

While three sensors 32,34 and 36 are shown embedded within header 20 in FIG. 1, the invention is not limited to a particular number of sensors. For example, in certain applications, only a single sensor may be required or desirable. In other instances, more than one of the same kind of sensor may be employed in the header 20. In such instances, the plurality of sensors may be employed to provide a differential measurement of the sensed physiological parameter. Alternatively, or in addition to such an arrangement, an additional sensor of the same type may be employed as a backup or redundant sensor, so as to delay or eliminate the need for surgical intervention that might otherwise be required to replace the implantable device 10 should critical sensors fail.

It should also be understood that the invention may include more than a single type of sensor embedded within header 20. For example, referring to FIG. 1, sensors 32 and 34 may be used to detect blood oxygen saturation, while sensor 36 may be a temperature sensor or a sensor for measuring the rate of blood flow. The types of sensors that may be embedded within header 20 are numerous; the type and number of sensors positioned within header 20 are limited only by the size of the implantable device 10 and header 20.

Figure 3:
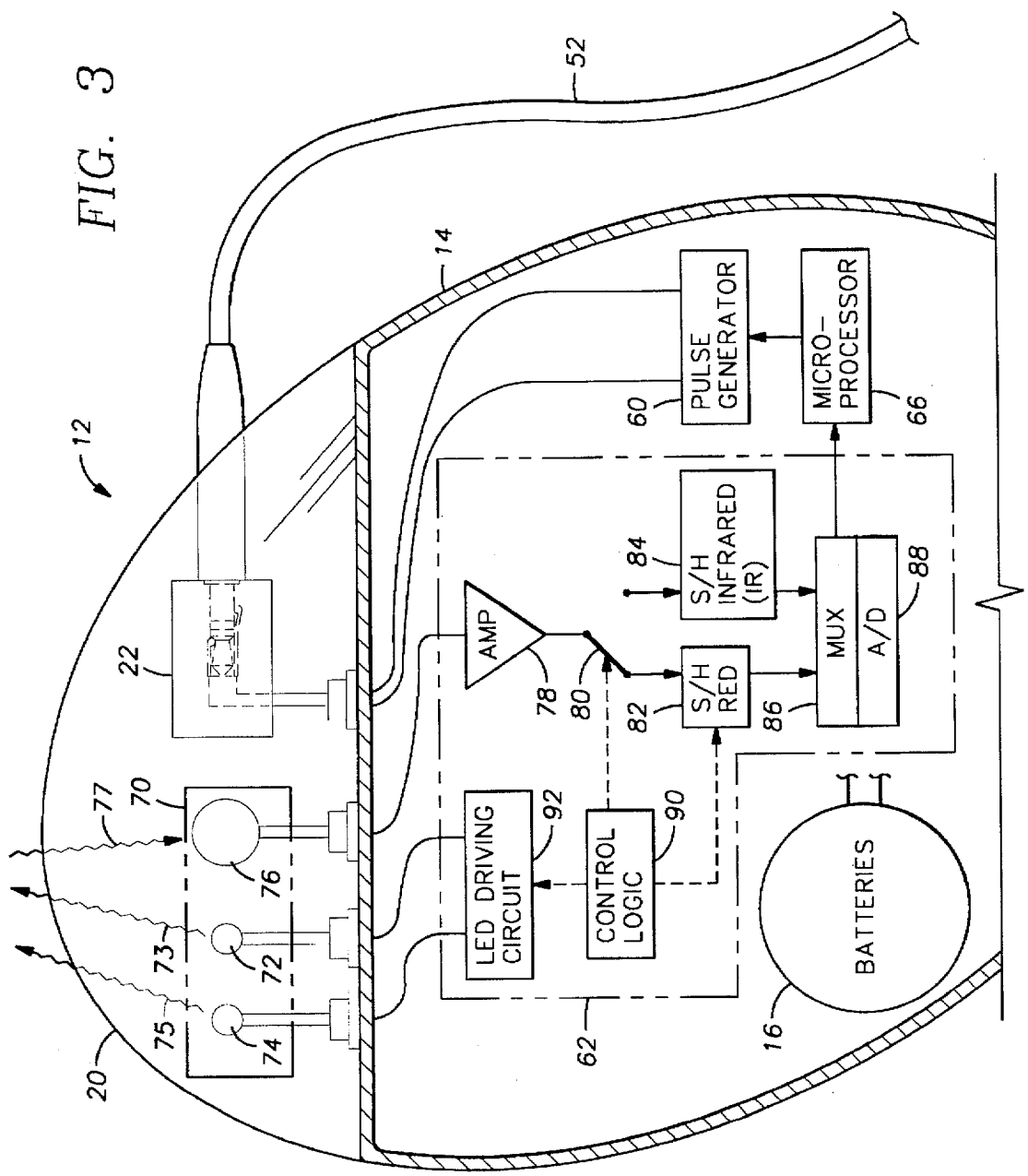
FIG. 3 is a schematic block diagram of another embodiment of the present invention employing an oximetry sensor embedded within the header of the pacer shown in FIG. 1.

There is shown in FIG. 3 a more particular embodiment of the invention in which a number of electroptic devices or other devices for emitting and sensing electromagnetic radiation are embedded within a translucent or transparent header of an implantable device 10 for emitting and receiving signals corresponding to sensed physiological parameters. For convenience, this embodiment of the invention also will be described for use with a pacer 12, the specifics of which were previously discussed. It is to be understood, of course, that this invention can similarly be used in a drug delivery system or any other implantable device.

Referring now to FIG. 3, pacer 12 includes an oximetry sensor 70 for detecting the level of oxygen saturation in the blood. More specifically, oximetry relates to the portion of circulating hemoglobin that has been saturated with oxygen. The extent of oxygen saturation is dependent upon the patient's level of activity, and the exchange process between carbon dioxide and oxygen within the blood. The relationship between oxygen saturation of the blood and the pulse rate of a patient having a healthy heart is well understood. Due to this relationship, the present invention may be employed to regulate the pacing rate in response to the sensed blood oxygen level in order to pace the heart at a rate appropriate to the physiological demands of the patient's body.

Oximetry sensor 70 is encapsulated within header 20 and includes photoemitters 72,74 and photodetector 76. In a preferred embodiment, the photoemitters 72,74 comprise light emitting diodes (LED's). More particularly, LED 72 is chosen to emit light in the red wavelength, for example within the range of 640–660 nm, while photoemitter 74 emits light in the infrared wavelength, such as a wavelength at the isobestic point (approximately 805 nm) or farther into the infrared spectrum, such as within the range of 880–940 nm. LED's 72,74 will be sequentially turned on and off so as to emit light pulses 73,75 in an alternating fashion. Photodetector 76, which may be a conventional phototransistor or photodiode, will receive the optical signals 77 that are reflected from the patient's blood. Thus, the output of photodetector 76 will represent a received signal first from the firing of the red LED 72 and subsequently from the IR LED 74.

In the embodiment of the invention shown in FIG. 3, sensor evaluation and control circuitry 62 includes circuitry for firing the LED's 72,74 in the proper sequence, and for separately receiving and evaluating the reflected signals. More specifically, sensor circuitry 62 includes an LED driving circuit 92, control logic 90, amplification circuit 78, switch 80 and sample-and-hold circuits 82,84. According to a predetermined sequence, the control logic circuit 90 will signal LED driving circuit 92 to alternately fire LED's 72,74, circuits 90 and 92 being powered by battery 16. The light pulses 73,75 alternately emitted by LED's 72,74, respectively, will be reflected back and received by photodetector 76 as reflected signal 77. The signal 77 received by photodetector 76 is amplified by a conventional amplification circuit 78. A switch 80 is controlled by control logic 90 so as to supply the amplified signal received from photodetector 76 alternately to the appropriate sample-and-hold circuits 82,84, circuit 82 holding the sensed value as detected by the reflection of red light emitted by LED 72, and circuit 84 holding the sensed value as detected by the reflection of IR wavelengths as emitted by LED 74. The outputs from sample-and-hold circuits 82,84 are provided to a multiplexer 86 which multiplexes the amplified output signal and supplies the signal to an analog-to-digital converter 88. The convened digital signal then is supplied to microprocessor 66 which, in accordance with a preprogrammed algorithm, causes pulse generator 60 to produce the appropriately timed stimulation to the patient's heart.

Other circuitry for receiving and processing signals received by photodetectors, and for thereafter generating appropriate pacing signals in a predetermined manner are known in the art of pulse oximetry. For example, U.S. Pat. No. 4,903,701, incorporated herein in its entirely, discloses circuitry associated with oxygen sensor control and pacemaker timing, the powering of the oxygen sensors, telemetry of the sensed oxygen saturation values, timing of sensor operation and the decoding of the signals generated by the oxygen sensor. Thus, the present invention is not limited to the exemplary circuitry described with reference to FIG. 3.

To enable the pulse oximetry sensor 70 thus described to operate effectively, it is important that the header 20 permit the desired wavelengths of light to pass through the header with an optical transmission effective rate of 70%. Accordingly, it is preferred that the material from which header 20 is formed have the following characteristics: high dielectric constant and dielectric strength, USP Class VI biocompatibility, flatness of its optical transmission curve encompassing the desired wavelength, and low changes in optical properties throughout implant life.

Presently, the most preferred materials for header 20 are Emerson & Cuming Stycase® 1267 or 1269 transparent, high-impact casting resins or Epoxy Technology, Inc. Epotek® 301 spectrally transparent epoxy which have an appropriate transmission between 900 nm and 350 nm.

Thus, the oximetry sensor 70 and cardiac pacer 12 shown in FIG. 3 provides the advantages offered by pulse oximetry technology but, in contrast to the prior art which typically required specialized leads for housing the LED's and photoreceptors, instead provides a self-contained integrated package that is not susceptible to the mechanical stresses imparted to conventional pacing leads. The oximetry sensor 70 and pacer 12 include windowless enclosures and thus are less likely to experience seal failures or to be infiltrated by corrosive and destructive body fluids.

Another alternative embodiment of the present invention that is useful when employing photoemitters and photodetectors as sensors is shown in FIGS. 4–7 in which one or more electromagnetic focusing devices 94 are embedded in or formed in or on header 20. Referring first to FIGS. 4 and 5, focusing device 94 may comprise a preformed lens 96 of glass or other composition. Lens 96 is positioned adjacent the outer surface 95 of header 20 when header 20 is formed such that reflected optical signals 77 are better focused on photodetector 76. More particularly, lens 96 is selected and positioned within header 20 such that its focal point is positioned on the light sensing surface 71 of photodetector 76. Similarly, lenses 97 are retained within header 20 adjacent outer surface 95 so as to more precisely focus the light emitted by LED's 72,74 at a focal point a predetermined distance from header surface 95.

Referring now to FIGS. 6 and 7, focusing device 94 may similarly comprise a Fresnel lens 99 that is created by forming a series of concentric grooves 98 on surface 95 of header 20. Grooves 98 may be laser etched or otherwise engraved on the header surface 95 and, like lens 96 shown in FIGS. 4 and 5, will serve to focus the reflected light signal 77 on the light sensing surface 71 of photodetector 76. Although not shown, a similar lens 99 is preferably formed in header 20 adjacent to LED 72,74 to more precisely focus the light pulses emitted from LED's 72,74.

While two distinct electromagnetic focusing devices 94 have been shown in FIGS. 4–7, it should be understood that the present invention is not limited to the use of the lenses 96 or 97. Instead, any of a variety of other means to focus electromagnetic energy may similarly be employed. For example, a disk of transparent or translucent material having a different index of refraction than the remainder of header 20 may likewise be used as a focusing device 94 and embedded within or otherwise retained on header 20.

When employing pulse oximetry technology, it is the ratio between oxygen saturation of the arterial blood flow, and that of the venous return flow, that is important in determining whether the patient's heart is functioning properly. See e.g. Inbar, et al. "Development of a Closed-Loop Pacemaker Controller Regulating Mixed Venous Oxygen Saturation Level", IEEE Trans. BME 35(9) (1988), at 679–690. The oximetry sensor distinguishes the arterial blood flow by sensing the pressure pulses created in the arterial blood flow by the periodic contraction of the heart. Conventional pulse oximetry sensors are motion intolerant in that movement of the oximetry sensor, as may, for example, be caused by a patient jogging or otherwise exercising, may cause the sensor to provide a signal similar to that caused by the arterial pressure pulses. This is because such exertion may cause relative movement between the sensor and the surrounding tissue. Such motion affects the thickness of tissue between the light source and photodetector, therefore altering the absorption of light as it travels along the light path. Repetitive motion may mimic arterial pulsation such that the oximetry sensor is unable to discern the difference between pulses resulting from motion and those resulting from the arterial activity. However, by positioning photoemitters 72,74 and photodetectors 76 in the header 20 of implantable device 10 as described here below, a differential measurement may be taken which can eliminate the problems that sensor motion may cause in conventional oximetry sensors.

Figure 8:
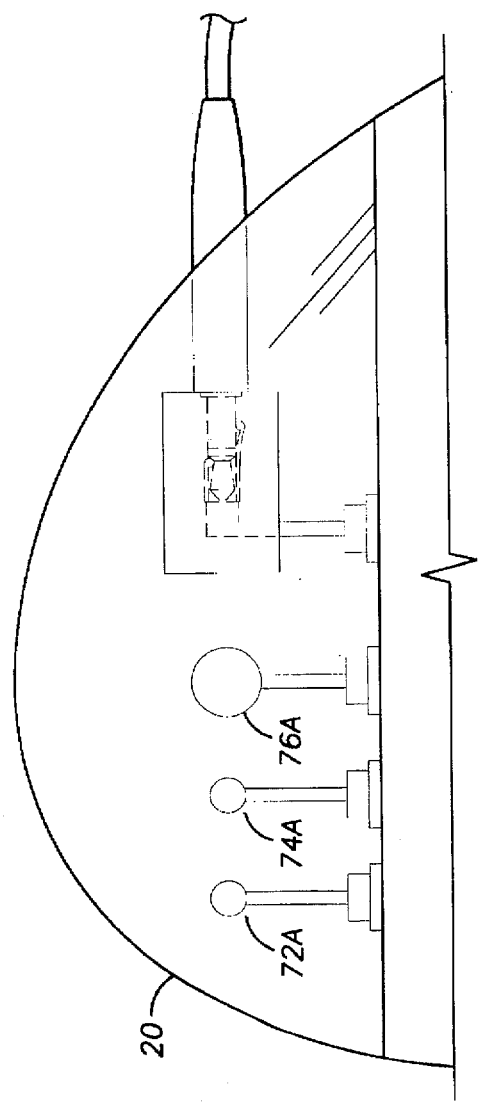
FIG. 8 is a partial elevational view of still another alternative embodiment of the present invention having an oximetry sensor embedded within the header of an implantable device.
Figure 9:
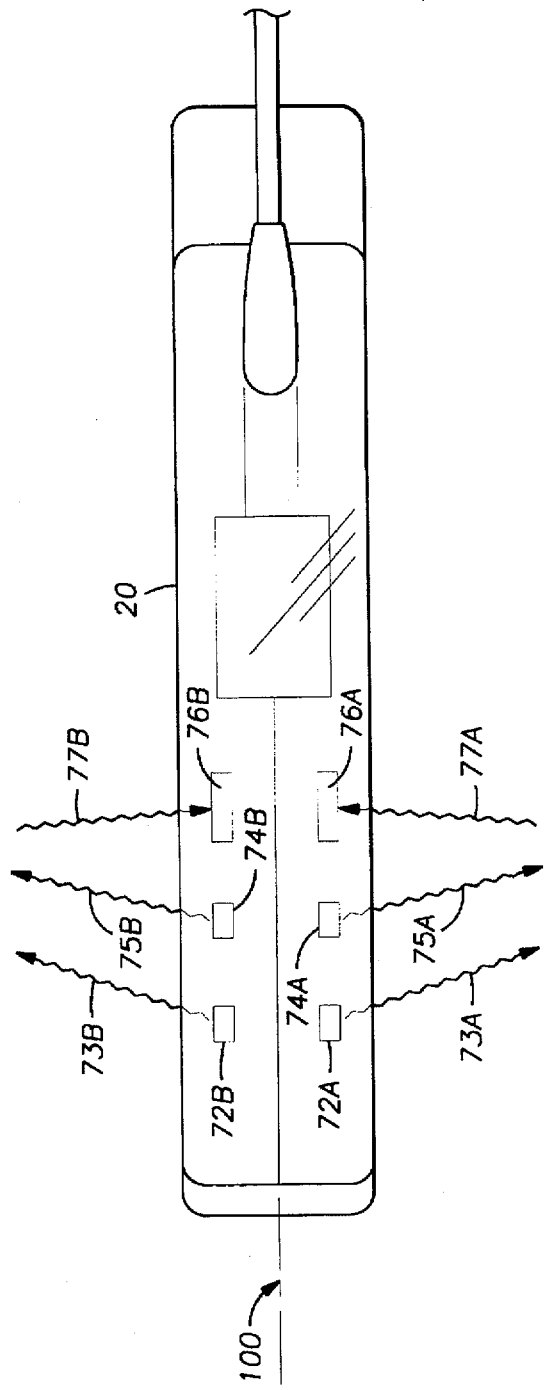
FIG. 9 is a top view of the implantable device shown in FIG. 8.

More specifically, and referring to FIGS. 8 and 9, two pairs of LED's 72,74 and two pairs of photodetectors 76 are positioned such that LED's 72a,74a and photodetector 76a face in a first direction relative to a plane 100 which bisects the pacer 12, while LED's 72b,74b and photodetector 76b face in the opposite direction. In this manner, optical signal 77a detected by photodetector 76a may be compared by microprocessor 66 (FIG. 3) to optical signal 77b detected by photodetector 76b for each. Through this comparison, the effect that movement of the pacer 12 would otherwise have on the sensed signals can be eliminated. A simple algorithm used to process these signals in order to eliminate the effects of movement would add the digitized signals detected by photodetectors 76a and 76b while LED's 72a and 72b are on. The same would be done when LED's 74a and 74b are on, providing the two signals necessary for calculating oxygen saturation throughout the blood flow cycle.

Figure 10:
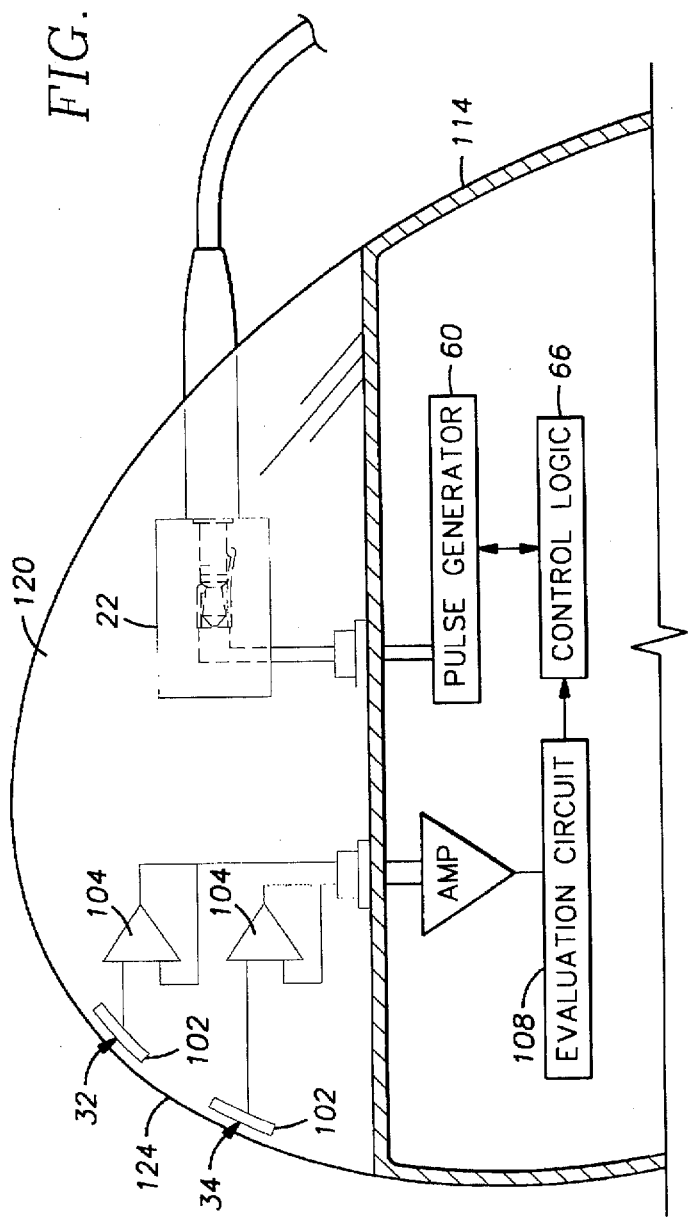
FIG. 10 is a schematic block diagram showing another alternative embodiment of the present invention having conductive plates embedded within the header of an implantable device.

Another embodiment of the present invention is shown in FIG. 10. As previously discussed, the invention is not limited to any particular type of sensor, but instead may be employed with any device capable of detecting or measuring a physiological parameter useful in properly stimulating the heart or dispensing needed medication or providing other desirable treatment. In certain instances, it may be advantageous to detect the electrocardiogram of a patient or otherwise make use of a body's tissues and fluids as a bioelectrode in order to measure a physiological parameter. In the embodiment shown in FIG. 10, sensors 32,34 comprise electrodes formed by conductive plates 102 that are embedded within header 120 of pacer 12. Header 120 is formed of an electrically insulative material having a relatively high dielectric constant. Plates 102 form capacitively-coupled bioelectrodes to sense electrical signals that are related to a desired physiological parameter.

As shown schematically in FIG. 10, plates 102 are disposed at a predetermined distance from outer surface 124 of header 120 and are connected to high input impedance buffers 104 which, for example, may be J-FET unity-gain buffers or single FET transistors. Because of their small size, buffers 104 may be mounted within header 120 immediately adjacent to places 102. Alternatively, buffers 104 may be included as part of the circuitry housed within housing 114. The outputs of buffers 104 are connected to an amplification circuit 106 which provides a signal to sensor evaluation circuit 108. The output from evaluation circuit 108 is communicated to a microprocessor or control logic 66. Depending upon predetermined instructions programmed into the control logic 66, the appropriate stimulating pulse will then be generated by pulse generator 60.

Figure 11:
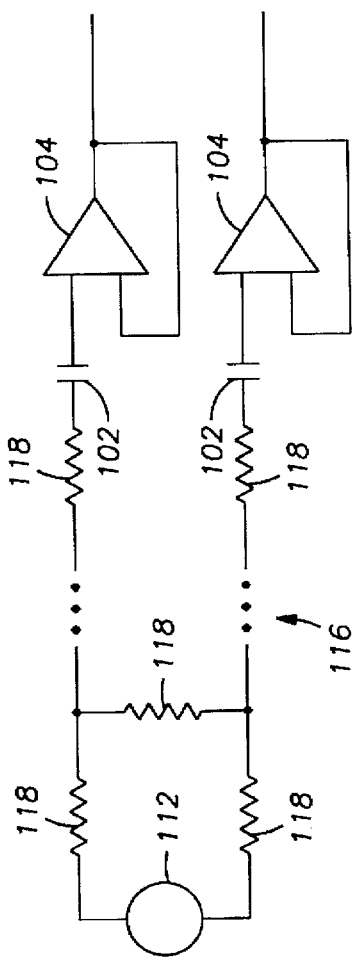
FIG. 11 is a schematic diagram showing the equivalent circuit corresponding to a portion of the circuit shown in FIG. 10.

FIG. 11 schematically depicts the equivalent circuit for the sensors 32,34 shown in FIG. 10. Bioelectric source 112 may, for example, represent the electrocardiogram which is capacitively coupled to plates 102 by a network 116 which represents the impedances 118 formed by the patient's blood and various tissues and the dielectric material from which the header 120 is formed. To provide for the appropriate capacitive coupling, it is important that the volume resistivity of the header material be higher than $1 \times 10^{12}$ ohm-cm. When used in a pacer 12 as shown in FIGS. 10 and 11 and used to sense the electrocardiogram, the header material preferably will have a dielectric constant above 3 (such as, for example 3.8), a volume resistivity above $1 \times 10^{12}$ ohm-cm and the electrodes 102 will be disposed approximately 0.2 mm from the outer surface 124 of header 120. An epoxy that is particularly suited for use in forming header 120 is Emerson & Cuming Stycast® 1267.

Alternatively, where a particular physiological parameter may be better sensed by means of a resistive coupling, rather than through the capacitive coupling just described, the material of header 120 may be selectively modified to have a lower dielectric constant. For example, electrically conductive particles such as colloidal platinum may be added to an epoxy header material before it sets, such that the hardened material will have a resistivity of approximately 1 megaohm-cm.

As stated above, the present invention may also be employed in implantable, closed-loop drug delivery systems. Conventional such systems are typically one of two types. A first such system is one having a sensor that is implanted remotely from the implantable drug delivery device. An example of such apparatus is disclosed in U.S. Pat. No. 5,041,107, the disclosure of which is incorporated herein by this reference. A second type of implantable system is structured such that the sensor is housed along with the drug delivery apparatus. An example of this second type of drug delivery system is shown in U.S. Pat. No. 4,373,527, the disclosure of which is also incorporated herein by reference.

Referring now to FIG. 12, there is shown implantable drug delivery system 130 which generally includes sensor body 132, electrically operable drug delivery mechanism 134 and catheter 136 disposed therebetween. Sensor body 132 generally includes a container 14 which houses battery 16 and hybrid circuit 18 all as previously described with reference to FIG. 3. Sensor body 132 further includes a header 20, also previously described with reference to FIG. 3. Header 20 seals and insulates physiological parameter sensors 138,139,140 as well as terminal 22. The hybrid circuit 18 includes sensor evaluation circuit 141, memory component 142, microprocessor 144 and a pulse generator 146.

The configuration of sensor evaluation circuit 141 is dependent upon the type of physiological parameter sensors 138–140 that are employed. In turn, the choice of physiological parameter sensors 138–140 will, in part, be dependent upon the particular drug that is to be administered via implantable drug delivery/system 130. Although the present invention is not limited to any particular implantable drug delivery system, it may be used advantageously in an implantable insulin delivery system. The determining factor in whether to administer insulin is the measure of glucose circulating in the patient's bloodstream. As with oxygen saturation, measurements of circulating glucose may be made by photoelectric means. For example, in the implantable system 130 shown in FIG. 12, devices 138 and 139 may be LED's 148,150 chosen to emit light in the wavelengths of 9.68 micrometers and 3.42 micrometers, respectively. Sensor 140 may comprise phototransistor which will receive reflected light from that emitted by LED's 148,150. The signals from phototransistor 139 may be sampled by sensor evaluation circuit 141 which, in this embodiment, would be substantially identical to the sensor evaluation circuit 62 described with reference to FIG. 3. Based on the values sensed and evaluated, microprocessor 144 will cause pulse generator 146 to generate an electrical pulse that will be transmitted through the conductors contained in catheter 136 to drug delivery mechanism 134 which will dispense the appropriate amount of insulin response thereto.

Figure 14:
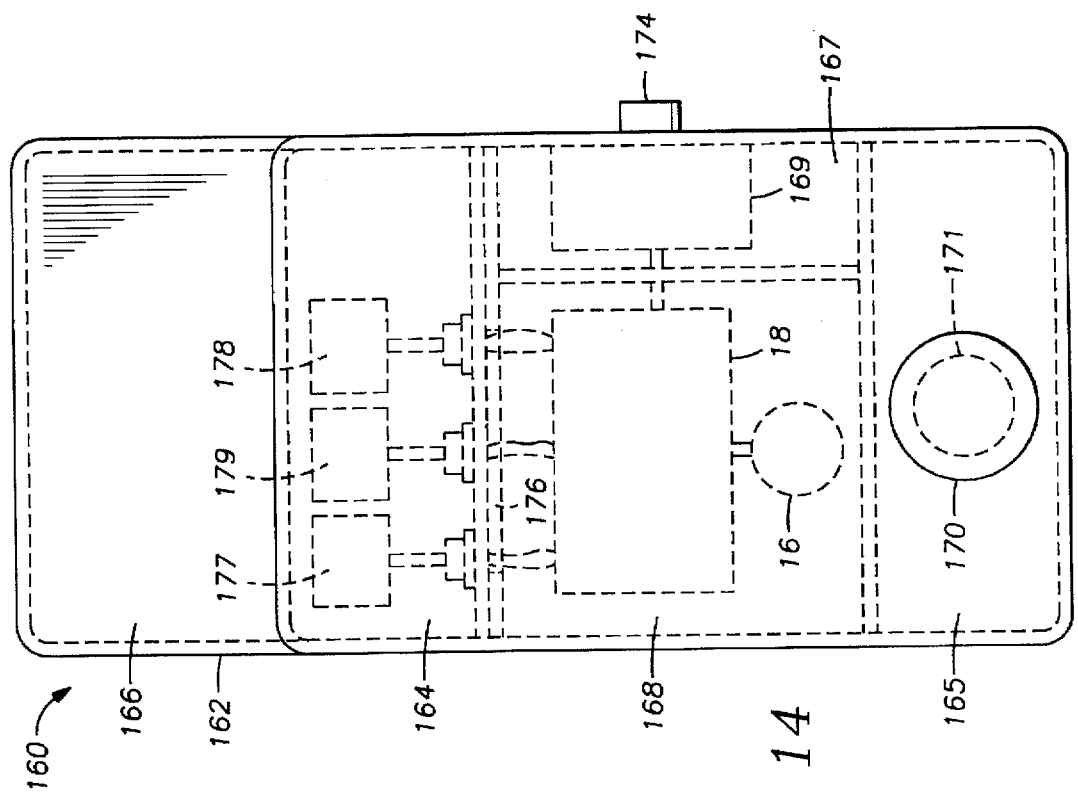
FIG. 14 is a top view of the drug delivery system shown in FIG. 13.
Figure 13:
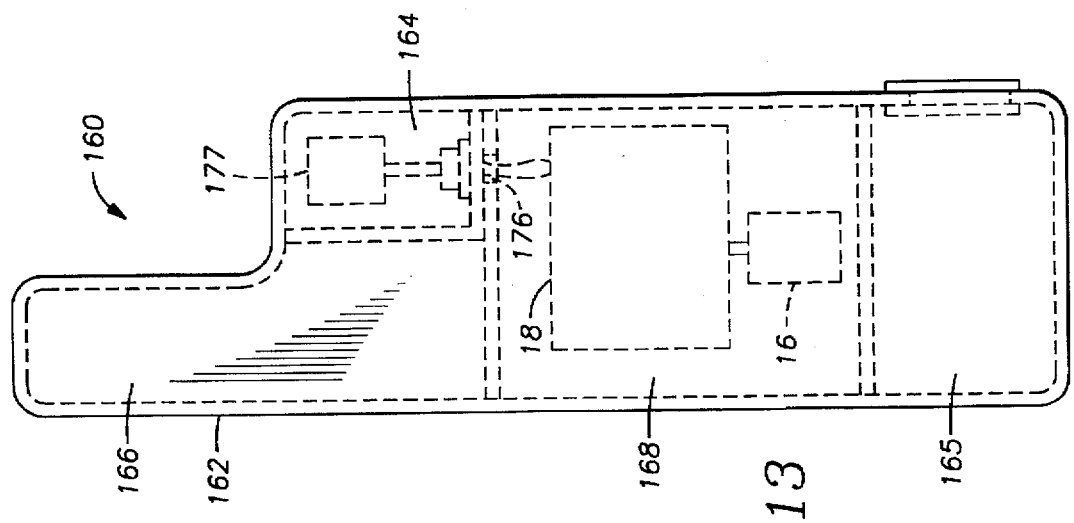
FIG. 13 is an elevational view of another alternative embodiment of the present invention employed in another type of implantable drug delivery system.

A drug delivery system of the type having the sensor housed with the drug delivery apparatus and which employs the present invention is shown in FIGS. 13 and 14. As shown, implantable drug delivery system 160 generally includes container 162 and header portion 164.

Container 162 is made of a biocompatible material such as stainless steel or titanium and is generally divided internally into four compartments or chambers: an inlet chamber 165; a reservoir chamber 166; a pump chamber 167; and an electronics chamber 168. Inlet chamber 165 contains a supply port 170 which includes a self-sealing membrane 171. To supply insulin or other appropriate drug to drug delivery system 160, the drug is injected by means of a hypodermic needle that is inserted through membrane 171. Inlet chamber 165 is in fluid communication with reservoir 166 and, when required, the drug will be drawn from inlet chamber into reservoir 166 through a fluid duct (not shown). Pump chamber 167 includes a pump 169 which, when receiving the appropriate signal from the circuitry contained within electronics chamber 168, will pump the appropriate amount of medication from reservoir chamber 166 into the patient's body via port 174.

Housing 162 includes an aperture 176 (FIG. 14) into electronics chamber 168. Header 164 closes aperture 176 and seals the physiological parameter sensors 176,177,178 therein. Electronics chamber 168 houses batteries 16 and hybrid circuit 18. The hybrid circuit 18 contains the sensor evaluation circuitry, memory, microprocessor and pulse generator as previously described with reference to FIG. 12.

As described previously, the invention may be employed with any of a variety of physiological parameter sensors. Where such sensors employ LED's and phototransistors or other photoelectric means, the material used in forming header 164 will be selected to as to have the optical properties necessary to achieve the desired light transmission. For example, an epoxy having the physical characteristics described previously with reference to header 20 in FIG. 3 is well suited for use in the implantable drug delivery system shown in FIGS. 13 and 14.

Figure 15:
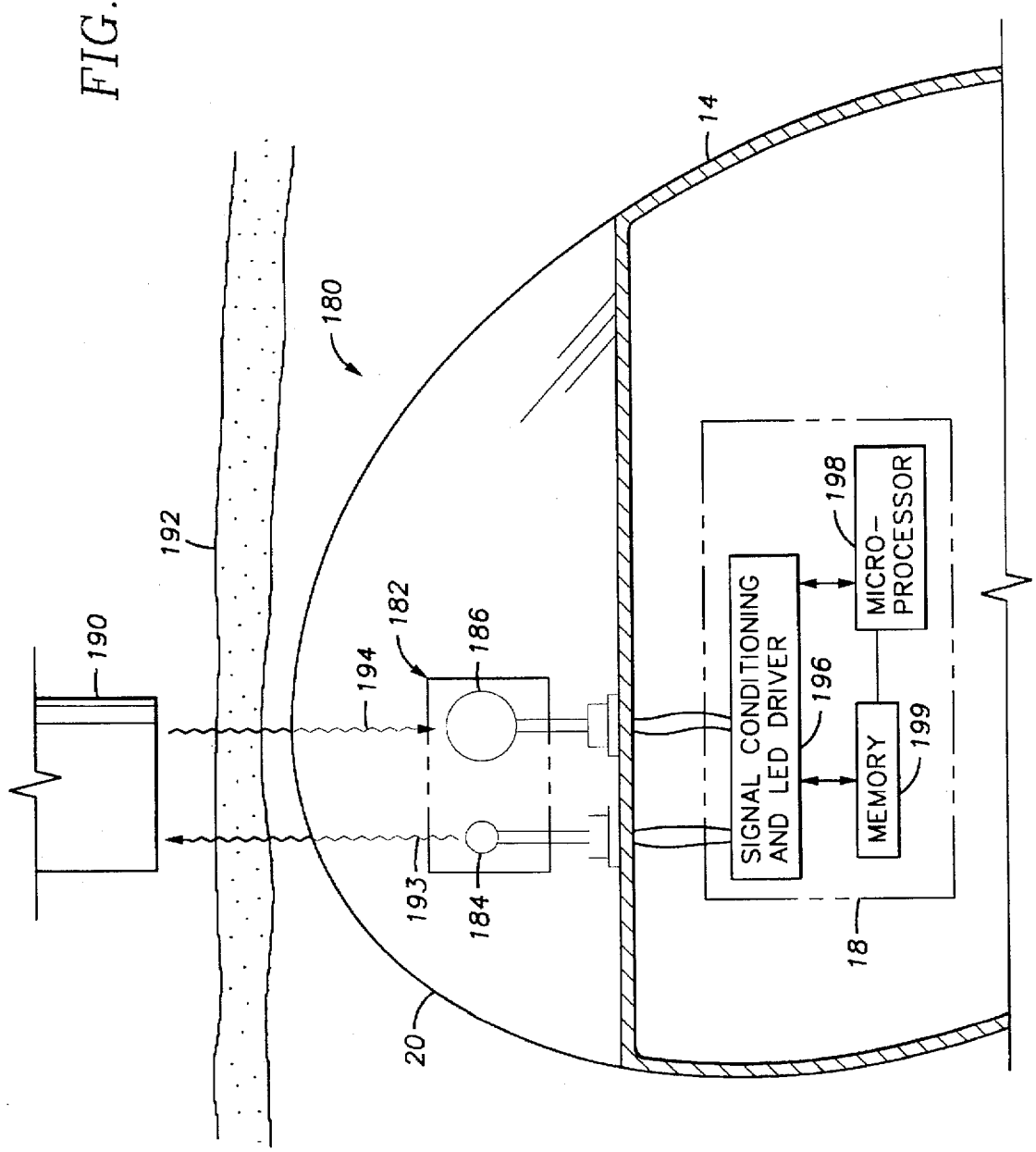
FIG. 15 is a partial elevational view of another alternative embodiment of the present invention with certain components shown in a schematic block diagram form.

The principles of the present invention can also be employed as a telemetry link used to transmit data or instructions to and from the implantable device. Referring to FIG. 15, implantable device 180 is shown having a container 14 and header 20. Container 14 houses a battery (not shown) and a hybrid circuit 18 which contains the electronics required both to fulfill the primary function of the implantable device, for example, cardiac pacing or drug delivery, as well as the components required to communicate between the implantable device and data transmitters and receivers that may be located both outside the body or implanted remotely from the implantable device 180. The telemetry link 182 is contained within header 20 and can comprise any of a number of types of transmitters and receivers, the details of which will depend on the type of communications desired. Particularly suited for use in the present invention is communication link 182 which employs a photoemitter such as LED 184 and a photodetector such as phototransistor 186. LED 184 and phototransistor 186 permit an optical link between implantable device 180 and external probe 190 that, when placed against the patient's skin 192 at a location adjacent to header 20 can transmit instructions via optical signal 194. Those instructions are received at photodetector 186 and transmitted to signal conditioning and LED driver circuitry 196, the output of which may be used to reprogram microprocessor 198 or be stored in memory package 199. Similarly, data gathered by implantable device 180 may be transmitted to probe 190 by means of LED 184 which, in response to the appropriate signal from microprocessor 198 and signal conditioning and LED driver circuit 196, will transmit optical signal 193 to probe 190. As will be understood by those skilled in the art, where implantable device 180 includes a telemetry link 182 as thus described, header 20 should have the optical qualities and properties such as those previously described for header 20 shown in FIG. 3. It should also be understood that the telemetry link 182 is not limited to a photoelectric means, but instead may send and receive telemetry by other means, for example, by transmission of radiofrequency signals, in which event, antennas, rather than photoemitters and photodetectors, would be employed in header 20. Similarly, the invention is not limited to a means for communicating with an external probe 190, but instead may be configured to communicate with other remotely positioned implantable devices that may, for example, include physiological parameter sensors such as contemplated in U.S. Pat. No. 4,886,064.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A pulse oximetry sensor comprising:
   a first pulse oximeter including a first photodetector having a light-sensing surface;
   a second pulse oximeter including a second photodetector having a light-sensing surface; and
   a body encapsulating and sealing said first and said second pulse oximeters in a predetermined orientation such that said light-sensing surfaces of said first and second photodetector face in different directions.

2. The sensor of claim 1 wherein said sensor apparatus comprises a telemetry transducer for communicating with a device remote from said sensor.

3. The sensor apparatus of claim 1 wherein said body is made of epoxy.

4. The sensor apparatus of claim 1 wherein said body is made of a ceramic material.

5. The sensor apparatus of claim 1 wherein said body is made of plastic.

6. The sensor apparatus of claim 1 wherein said body is made of glass.

7. The sensor apparatus of claim 1 wherein said body is translucent.

8. The sensor apparatus of claim 1 wherein said body is transparent.

9. The sensor apparatus of claim 1 wherein selected portions of said body are made of a material having a volume resistivity less than 10 megaohm cm.

10. The sensor apparatus of claim 1 wherein said body is made of a material having a volume resistivity higher than $1 \times 10^{12}$ ohm-cm.

11. The sensor apparatus of claim 1 wherein said body has a dielectric constant greater than 3.

12. The sensor apparatus of claim 1 wherein said body has high optical transmissivity to wavelengths between 350 nanometers and 900 nanometers.

13. The sensor apparatus of claim 1 wherein said body has high optical transmissivity to wavelengths between 3 micrometers and 10 micrometers.

14. The sensor apparatus of claim 1 wherein said first and second photodetector is capable of receiving through said body an optical signal indicative of the measure of oxygen content in a substance outside said body.

15. The sensor apparatus of claim 1 wherein said sensor further comprises a photoemitter capable of emitting through said body an optical signal to be received as reflected light by one or more of said first and second photodetectors.

16. The sensor apparatus of claim 1 wherein said sensor further comprises at least two photoemitters, each of said photoemitters capable of emitting through said body an optical signal to be received as reflected light by one or more of said first and second photodetectors.

17. The sensor apparatus of claim 1 further comprising an electromagnetic focusing device on said body.

18. The sensor apparatus of claim 17 wherein said electromagnetic focusing device comprises a material having an index of refraction that is different from the index of refraction of said body.

19. The sensor apparatus of claim 17 wherein said body includes an outer surface, and wherein said electromagnetic focusing device comprises a plurality of grooves formed in said outer surface of said body.

20. The sensor apparatus of claim 17 wherein said sensor includes a sensing surface, and wherein said electromagnetic focusing device comprises a lens attached to said body, said lens having a focal point adjacent to said sensing surface of said sensor.

21. The sensor apparatus of claim 1 wherein said body includes an outer surface, and wherein said sensor comprises a conductive plate disposed in said body a predetermined distance from said outer surface.

22. The sensor apparatus of claim 21 wherein said predetermined distance is within the range of approximately 0.1 mm to 2.0 mm.

23. A multiple sensor device comprising the sensor of claim 1 in combination with at least one non-oximetric sensor.

24. The multiple sensor device of claim 23 further comprising a telemetry link.

25. The sensor apparatus of claim 1 wherein said light-sensing surface of said first photodetector faces in a direction substantially 180 degrees apart from the direction faced by said light-sensing surface of said second photodetector.

26. A pulse oximetry sensor apparatus comprising:

a first pulse oximeter including a first photodetector having a light-sensing surface;

a second pulse oximeter including a second photodetector having a light-sensing surface;

a body encapsulating and sealing said first and said second pulse oximeters in a predetermined orientation such that said light-sensing surfaces of said first and second photodetector face in different directions, said body constructed of a material selected from the group consisting of epoxy, ceramic, plastic, or glass, such that said body is at least translucent;

wherein selected portions of said body are made of a material having a volume resistivity less than 10 megaohm cm;

wherein said body has a dielectric constant greater than 3;

wherein said body has high optical transmissivity to wavelengths between 350 nanometers and 900 nanometers;

a telemetry transducer for communicating with a device remote from said sensor; and a photoemitter capable of emitting through said body an optical signal to be received as reflected light by one or more of said first and second photodetectors;

wherein said first and second photodetector is capable of receiving through said body an optical signal from said photoemitter, indicative of the measure of oxygen content in a substance outside said body.

* * * * *